US012796928B2

(12) United States Patent
Sen et al.

(10) Patent No.: US 12,796,928 B2
(45) Date of Patent: Nov. 17, 2026

(54) COMMUNICATION AND POWERING SYSTEMS AND METHODS BETWEEN IMPLANTABLE AND WEARABLE DEVICES

(71) Applicant: PURDUE RESEARCH FOUNDATION, West Lafayette, IN (US)

(72) Inventors: Shreyas Sen, West Lafayette, IN (US); Baibhab Chatterjee, Newberry, FL (US); Mayukh Nath, Corning, NY (US); Arunashish Datta, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 150 days.

(21) Appl. No.: 18/840,759

(22) PCT Filed: Jan. 30, 2023

(86) PCT No.: PCT/US2023/011832
§ 371 (c)(1),
(2) Date: Aug. 22, 2024

(87) PCT Pub. No.: WO2023/163840
PCT Pub. Date: Aug. 31, 2023

(65) Prior Publication Data

US 2025/0176830 A1 Jun. 5, 2025

Related U.S. Application Data

(60) Provisional application No. 63/314,736, filed on Feb. 28, 2022.

(51) Int. Cl.
*A61B 5/00* (2006.01)
*H04B 13/00* (2006.01)

(52) U.S. Cl.
CPC .......... *A61B 5/0031* (2013.01); *A61B 5/6803* (2013.01); *A61B 5/686* (2013.01); *H04B 13/005* (2013.01)

(58) Field of Classification Search
CPC ... A61B 5/0002; A61B 5/0004; A61B 5/0006; A61B 5/0008; A61B 5/0011;
(Continued)

(56) References Cited

U.S. PATENT DOCUMENTS

2012/0197350 A1* 8/2012 Roberts ................ A61B 5/0028 607/60
2017/0095667 A1* 4/2017 Yakovlev ........... A61N 1/36071
(Continued)

OTHER PUBLICATIONS

Extended European Search Report for European Application No. 23760520.9, dated Feb. 12, 2026; 12 pages.
(Continued)

*Primary Examiner* — Robert L Nasser
(74) *Attorney, Agent, or Firm* — Hartman Global IP Law; Gary M. Hartman; Domenica N. S. Hartman

(57) ABSTRACT

A system includes a wearable device and an implantable device. The wearable device includes one or more signal transmitters and is configured to be positioned adjacent to or in contact with a human or animal body. The implantable device includes a signal receiver and is configured to be implanted onto or within the human or animal body. The one or more signal transmitters of the wearable device are configured to transmit the signals through the human or animal body to the signal receiver of the implanted device via a galvanic coupling operable using electro-quasistatic signal transmission. The system also includes a capacitive element positioned on an electrical current flow path of the galvanic coupling between at least one of the one or more signal transmitters and the signal receiver.

19 Claims, 8 Drawing Sheets

Implantable devices wont work with EQS Capacitive HBC

(58) Field of Classification Search
CPC . A61B 5/0015; A61B 5/0026; A61B 5/00287; A61B 5/0031
See application file for complete search history.

(56) References Cited

U.S. PATENT DOCUMENTS

| | | | | |
|---|---|---|---|---|
| 2018/0336967 | A1 | 11/2018 | Milevski et al. | |
| 2019/0273396 | A1 | 9/2019 | Shahmohammadi | |
| 2019/0373962 | A1 | 12/2019 | Datta et al. | |
| 2021/0026158 | A1 | 1/2021 | Miller | |
| 2021/0258080 | A1 | 8/2021 | Sen et al. | |
| 2022/0193427 | A1* | 6/2022 | Sen | A61N 1/37223 |

OTHER PUBLICATIONS

Chatterjee, B., et al, "A 1.15 μW 5.54mm Implant with a Bidirectional Neural Sensor and Stimulator SoC utilizing Bi-Phasic Quasistatic Brain Communication achieving 6kbps-10Mbps Uplink with Compressive Sensing and RO-PUF based Collision Avoidance", JSAP, Dated 2021 (2 Pages).

Cuevas, N., et al., "Modeling and Characterization of Intra-Body Links for a Smart Contact Lens", IEEE, Dated 2021 (5 Pages).

Jeon, Y. et al., "A 650-uW 30 Mbps Galvanic Coupling Communication Receiver for Bionic Arms", IEEE, Dated 2018 (5 Pages).

Wegmueller, M.S et al., "BPSK & QPSK Modulated Data Communication for Biomedical Monitoring Sensor Network", Proceedings of the 28th IEEE (2006), 4 pages.

International Search Report & Written Opinion for International Application No. PCT/US2023/011832, dated May 3, 2023 (13 pages).

* cited by examiner

Implantable devices wont work with EQS Capacitive HBC

COMMUNICATION AND POWERING SYSTEMS AND METHODS BETWEEN IMPLANTABLE AND WEARABLE DEVICES

CROSS REFERENCE TO RELATED APPLICATION

This application claims priority to International Patent Application No. PCT/US2023/011832 filed Jan. 30, 2023, which claims priority to U.S. Provisional Patent Application No. 63/314,736, entitled "Communication and Powering Systems and Methods Between Implantable and Wearable Smart Devices," which was filed Feb. 28, 2022. The contents of these prior patent documents are hereby incorporated by reference in their entirety.

GOVERNMENT RIGHTS

This invention was made with government support ECCS 1944602 awarded by the National Science Foundation. The government has certain rights in the invention.

TECHNICAL FIELD

The present disclosure in general relates to powering and communication between wearable and implantable devices. Particularly, the present disclosure demonstrates a low power communication and powering of implantable devices using human body communication (HBC).

BACKGROUND

This section introduces aspects that may help facilitate a better understanding of the disclosure. Accordingly, these statements are to be read in this light and are not to be understood as admissions about what is or is not prior art.

Remote communication between a controlling hub and a smart contact lens through traditional wireless body area network (WBAN) techniques operating in the radio frequency (RF) range, such as Bluetooth, is difficult-owing to the power consumption requirement of RF transceivers-making it hard to implement in a small form factor such as that of a contact lens. This necessitates the use of technologies that use lower power to operate, such as Human Body Communication (HBC). HBC uses the human body as a communication medium between multiple BAN devices. When operated in the quasistatic frequency range where the wavelength is large compared to the human body, HBC signals are confined within 5-15 cm of the body of the user, making it physically secure as well as power efficient compared to RF as RF signals would be broadcasted farther away from the user, thus wasting energy and compromising security. A well-studied mode of quasistatic HBC for wearable BAN devices is capacitive Electro Quasi-Static HBC (EQS-HBC). EQS-HBC, as shown in FIG. 1A, uses the human body as a forward path between a Tx an Rx, while relies on parasitic capacitive coupling between earth's ground and the device's ground plane for the return path. The availability of this return path coupling to Earth's ground is critical in successful operation of an EQS-HBC device, and this unfortunately makes it unusable for implantable devices where the implanted device's ground plate would be covered by the human body without a direct coupling to earth's ground. This is demonstrated in FIG. 1B by simulating an implanted capacitive EQS device, showing minimal leakage of fields outside the body. Same would hold true for a smart contact lens, where the device can be considered partially implanted—the ground plate would be covered by the eyelid when the eye is closed, and even otherwise would show a very weak coupling to the earth, due to its very small ground plane area—thus making regular EQS HBC communication impractical.

SUMMARY

Aspects of this disclosure describe systems and methods enabling low-power communications between an implantable and a wearable device. The systems and methods can improve physical security and decrease communication path loss by using galvanic EQS-HBC.

Specifically, the present disclosure includes aspects which can include a wearable device, and implantable device, and a capacitive element. The wearable device can include one or more signal transmitters and can be positioned adjacent to or in contact with a human or animal body. The implantable device can include a signal receiver and can be implanted onto or within the human or animal body. The one or more signal transmitters of the wearable device can be configured to transmit the signals through the human or animal body to the signal receiver of the implanted device via a galvanic coupling operable using electro-quasistatic signal transmission. The capacitive element can be positioned on an electrical current flow path of the galvanic coupling defined between at least one of the one or more signal transmitters and the signal receiver. Further, the capacitive element can be configured to restrict the flow of DC power between the at least one of the one or more signal transmitters and the signal receiver.

In some embodiments, the wearable device can include any one or more of a headset, necklace, headband, cap, helmet, spectacles, or headgear, and the implantable device can include any one or more of a contact lens, cochlear implant, implantable device inside a mouth, or neural implant inside a brain. In other embodiments, the wearable device can include a waist-mounted device and the implantable device can be positioned inside a stomach of the human or animal.

In other aspects, the capacitive element can include a series capacitor configured to restrict DC power being transmitted by the signal transmitter. In some embodiments, the series capacitor can be embedded within the wearable device. In other embodiments, the capacitive element can include one or more earpads configured to couple to an exterior of the wearable device, and the one or more earpads can include a dielectric material. In still other embodiments, the capacitive element can include one or more floating electrodes positioned adjacent to the human or animal body that can form an air gap operable to restrict the flow of the DC power.

In other aspects, the wearable device can include a first signal transmitter defined by two prongs positioned on the same side of a head of the human or animal, and the two prongs can be configured to generate a differential electric signal polarized vertically relative to a head of the human or animal. In other embodiments, the wearable device can include a signal transmitter defined by first and second prongs positioned on opposing sides of a head of the human or animal, and the first and second prongs can be configured to generate a differential electric signal polarized horizontally relative to the head of the human or animal.

In still other aspects, the implantable device can include a contact lens sized for placement onto an eye of the human or animal, and the contact lens can include a pair of electrodes positioned vertically or horizontally opposite to each other relative to the eye. The electrodes can be configured to receive differential electric signals.

This summary is provided to introduce a selection of the concepts that are described in further detail in the detailed description and drawings contained herein. This summary is not intended to identify any primary or essential features of the claimed subject matter. Some or all of the described features may be present in the corresponding independent or dependent claims, but should not be construed to be a limitation unless expressly recited in a particular claim. Each embodiment described herein does not necessarily address every object described herein, and each embodiment does not necessarily include each feature described. Other forms, embodiments, objects, advantages, benefits, features, and aspects of the present disclosure will become apparent to one of skill in the art from the detailed description and drawings contained herein. Moreover, the various apparatuses and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1A:
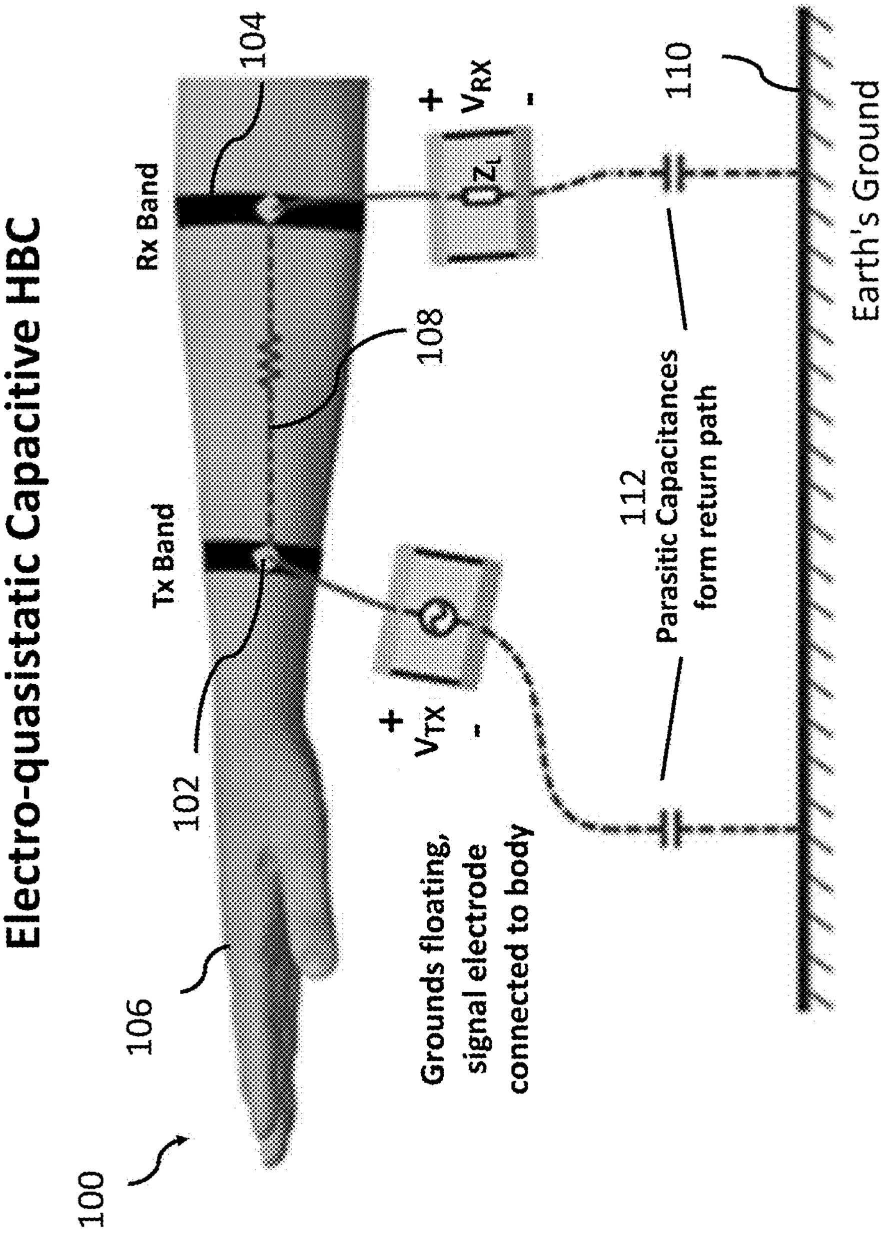
FIG. 1A depicts a capacitive EQS-HBC system utilizing body tissue as the medium of communication.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown, or the precise experimental arrangements used to arrive at the various graphical results shown in the drawings.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

The present disclosure relates to Wireless Body Area Network (WBAN) communication specifically from a wearable to an implantable device using electro-quasistatic (EQS) galvanic human body communication (HBC), hereinafter referred to as EQS-HBC. Galvanic EQS provides a low power and energy efficient methodology for HBC and, accordingly, may be utilized for data transfer between two wearable devices in contact with a human body. More specifically, galvanic EQS-HBC provides ultra-low power consumption in the EQS frequency range, is a physically secure communication method with low signal leakage out of body relative to prior art HBC methods, and provides a low communication path loss relative to prior art HBC methods (e.g., approximately 50 dB) for a broadband channel in the EQS range (e.g., approximately 10 kHz to 100 MHz).

In some embodiments, galvanic biphasic EQS-HBC may be utilized for communications between a smart contact lens and a headwear device (e.g., headphones, headband, or spectacles) as is illustrated and described herein. However, it should be understood that other forms of galvanic EQS-HBC devices may instead utilize the improved systems and methods described herein, and the technological improvements are not limited to smart contact lenses and headwear. Implantable devices may also include, for example, cochlear implants, implantable devices inside the mouth, or neural implants inside the brain. Still further, the wearable-implantable pair is not limited to a human or animal head, but can also be elsewhere on the body, for example, a waist mounted device (e.g., a belt) and an implantable device inside the stomach. As will be detailed herein, finite element method (FEM) based electromagnetic (EM) simulations may be utilized to validate the advantageous aspects of galvanic EQS-HBCs, showing low path loss of up to 50 dB.

Typical WBANs use radio frequency (RF) based communication methodologies such as Bluetooth, LoRa, ZigBee, and the like, each of which operates in a frequency band spanning hundreds of megahertz up to multiple gigahertz. Accordingly, the power consumption in these RF-based communication methodologies is high, for example, ranging from tens to hundreds of milliwatts. This high-power consumption of tens to hundreds of milliwatts for size-constrained nodes, such as nodes positioned on or inside a body, often depletes the battery quickly and requires frequent battery replacements. Further, the RF-based signals radiating away from the body at these high frequencies typically allow the data to be accessible as many as five to ten meters away from the devices which can compromise the security of the transmitted data. This motivates the need for a lower power and more secure communication methodology which can be used between two devices positioned near, on, or implanted within a body (e.g., a human or animal body) to increase battery lifetime for the size constrained nodes (e.g., smart contact lenses).

Using HBC, the body acts as a communication medium to carry data signals to a receiver. Operating HBC in the broadband Electro-Quasistatic (EQS) region has shown promise in terms of enhanced physical layer security. In the EQS domain of frequencies less than 100 MHz, the body acts like an antenna albeit with some inefficiencies. Thus, the signals may not be radiated efficiently away from the body in such a way to ensure that the signal is contained to within a short distance (e.g., approximately 0 to 10 centimeters) away from the body and therefore providing a physically secure channel for communication. Further, ultra-low power communication may be achieved by using HBC in the EQS domain, resulting in power consumption in the order of a few microwatts which is at least an improvement of around three orders of magnitude relative to traditional RF-based communication methods.

Figure 1B:
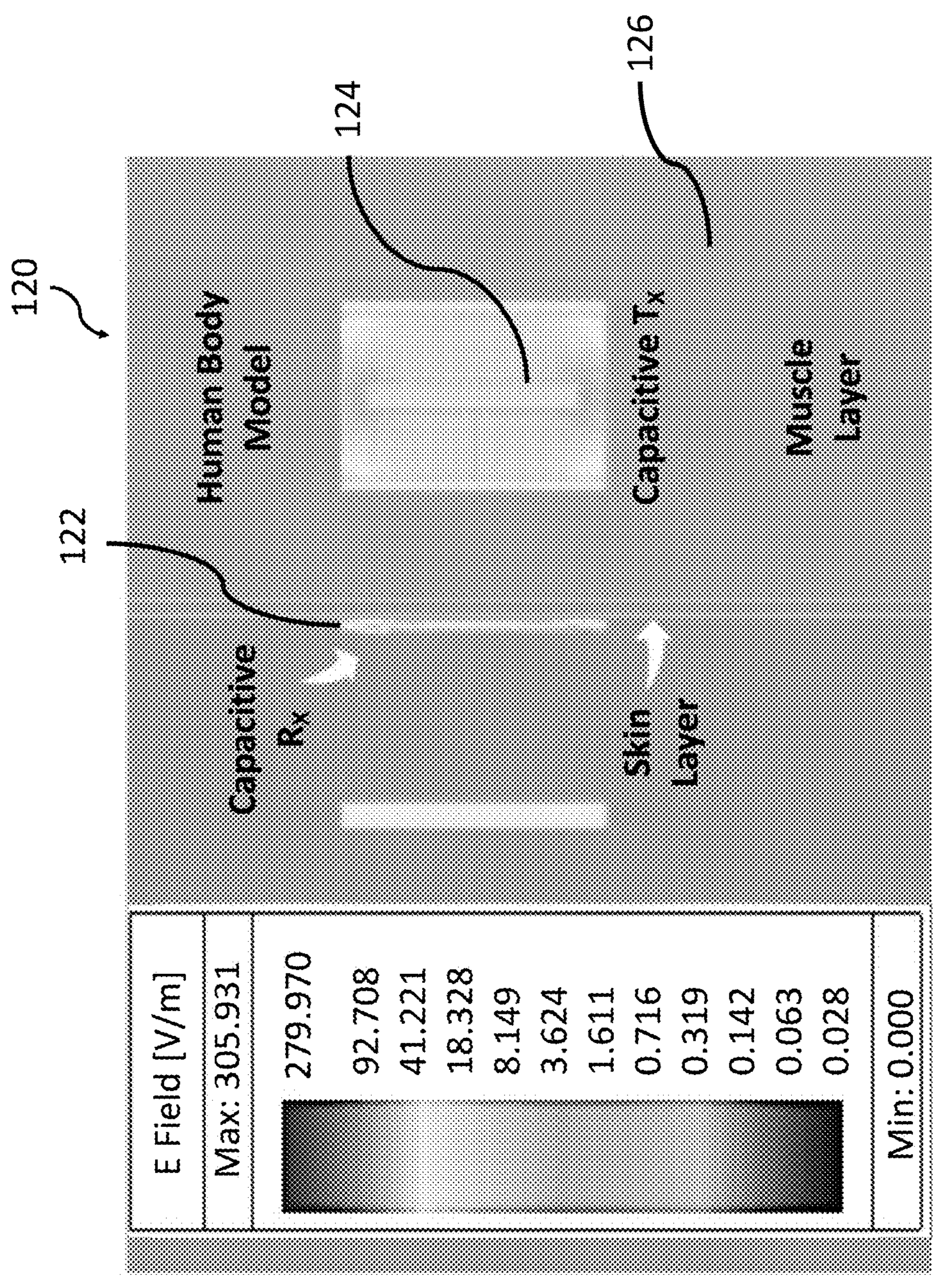
FIG. 1B depicts the incompatibility of a capacitive EQS-HBC system for wearables or implantable devices.

EQS-HBC can be operated in two primary alternative modalities: capacitive HBC or galvanic HBC. In capacitive HBC (100), as shown in FIG. 1A, signal electrodes (102, 104) (e.g., coils) connected to the body (106) provide for a forward electrical path (108) whereas the parasitic capacitance between the floating ground plate and the earth's ground (110) forms the return path (112) of the electrical circuit. However, as shown in the implantable device (120) illustrated in FIG. 1B, the absence of a direct path between the implanted electrodes (122, 124) to the earth's ground (not shown) results in the return path capacitance being approximately zero, and thus capacitive HBC is not functional. Specifically, the transmitter (124) having a floating ground plate is used to excite the human body (126), and the field leakage outside the body is minimal, which results in a very high path loss relative to galvanic HBC as will be described. These electrical path loss issues are also true for the use of a smart contact lens which can be considered as an implanted device as the device is covered by the eyelid when the eye is closed. Further, the small size of the device would also provide a very weak coupling to the earth's ground even when the eye is open and thus would result in a high path loss when capacitive HBC is used.

Figure 1C:
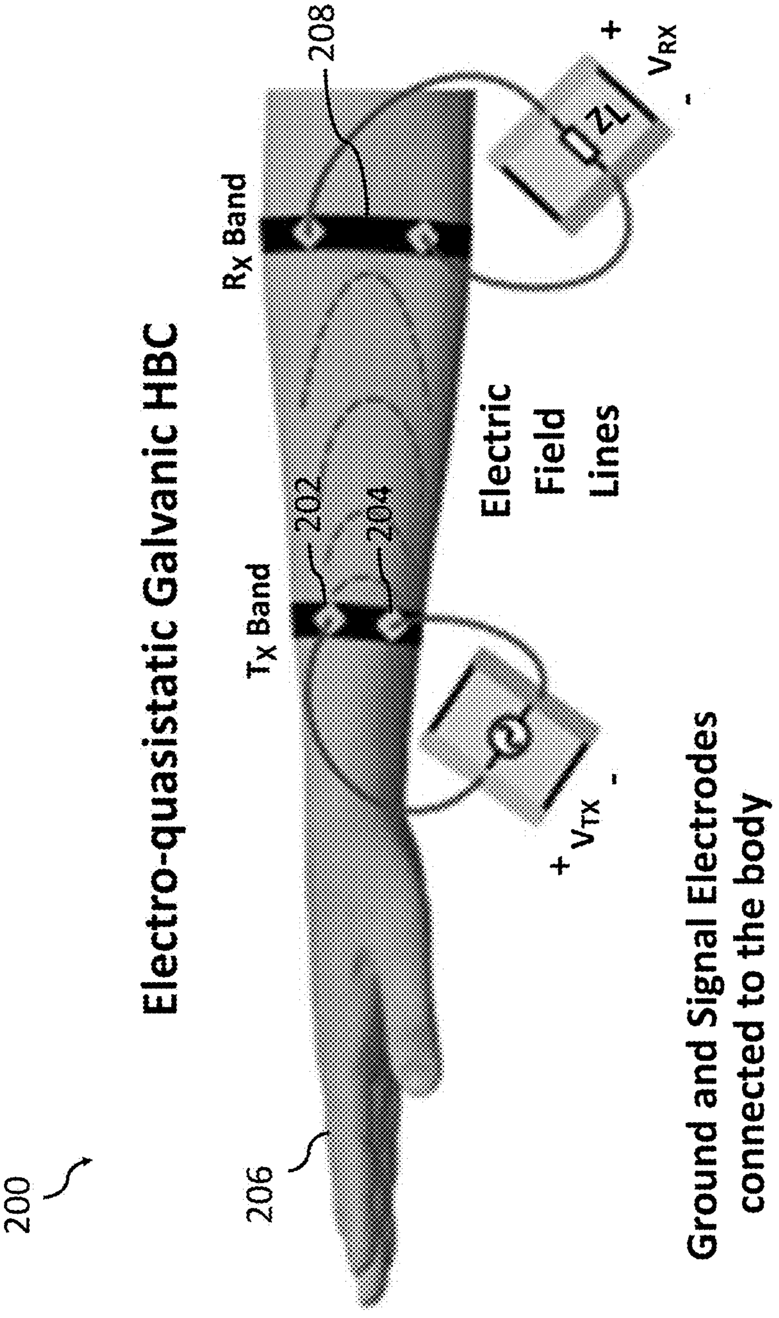
FIG. 1C depicts a galvanic EQS-HBC system utilizing body tissue as the medium of communication.
Figure 1D:
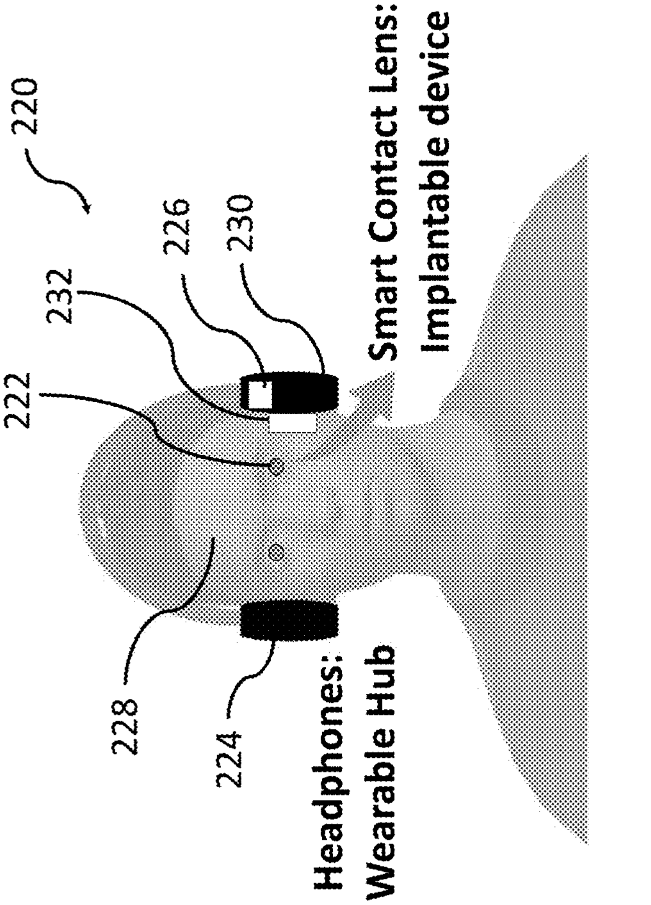
FIG. 1D depicts an example of a wearable galvanic EQS-HBC system, showing a headwear device in communication with a contact lens.

In galvanic HBC (200), as shown in FIG. 1C, the two electrodes (202, 204) (e.g., prongs, coils, etc.) of the transmitter are connected to the body (206) and the fringe fields passing through the body (206) are received by the receiver (208) (e.g., prongs, coils, etc.). More particularly, the transmitter can transmit information through the human body over a variable frequency to the receiver (208) when the variable resistance of the transmitter coil is tuned to the variable resistance of the receiver coil. This is advantageous in application of an implanted device as the two electrodes (202, 204) are surrounded by—and thus in contact with—the body (206). In one application (220), as shown in FIG. 1D, galvanic HBC may be utilized for communication between an implantable device (e.g., a smart contact lens (222)) and a wearable device such as a necklace, headband, headphones, cap, or helmet (e.g., headset (224)). Galvanic HBC, when utilized to transmit data between wearable and implantable devices, functions as a low loss channel (e.g., ~50 dB) as compared to the capacitive EQS-HBC methods described above.

To further reduce the power required for data transmission, a bi-phasic galvanic HBC is proposed where a capacitive DC blocking element (226) is positioned within the electrical signal path formed between the transmitter (i.e., the electrodes within the headset (224)) and the receiver (i.e., the electrodes within the smart contact lens (222)) to reduce or eliminate the DC power flowing through the body (228). In some embodiments, DC blocking element (226) may be a series capacitor embedded within the wearable device (e.g., within an ear portion of a headset). In other embodiments, DC blocking element (226) may take the form of one or more earpads (230) of a headset, the earpads including or being formed using a dielectric material configured to restrict the flow of the DC power between the transmitter and receiver, particularly when the transmitters include one or more prongs embedded within the ear portion of the headset as will be described in greater detail below. In still other embodiments, the DC blocking element (226) element may include one or more floating electrodes (232) positioned adjacent to the human or animal body, wherein the one or more floating electrodes (232) are configured to form an air gap operable to restrict the flow of the DC power between the signal transmitter and the signal receiver.

Figure 2A:
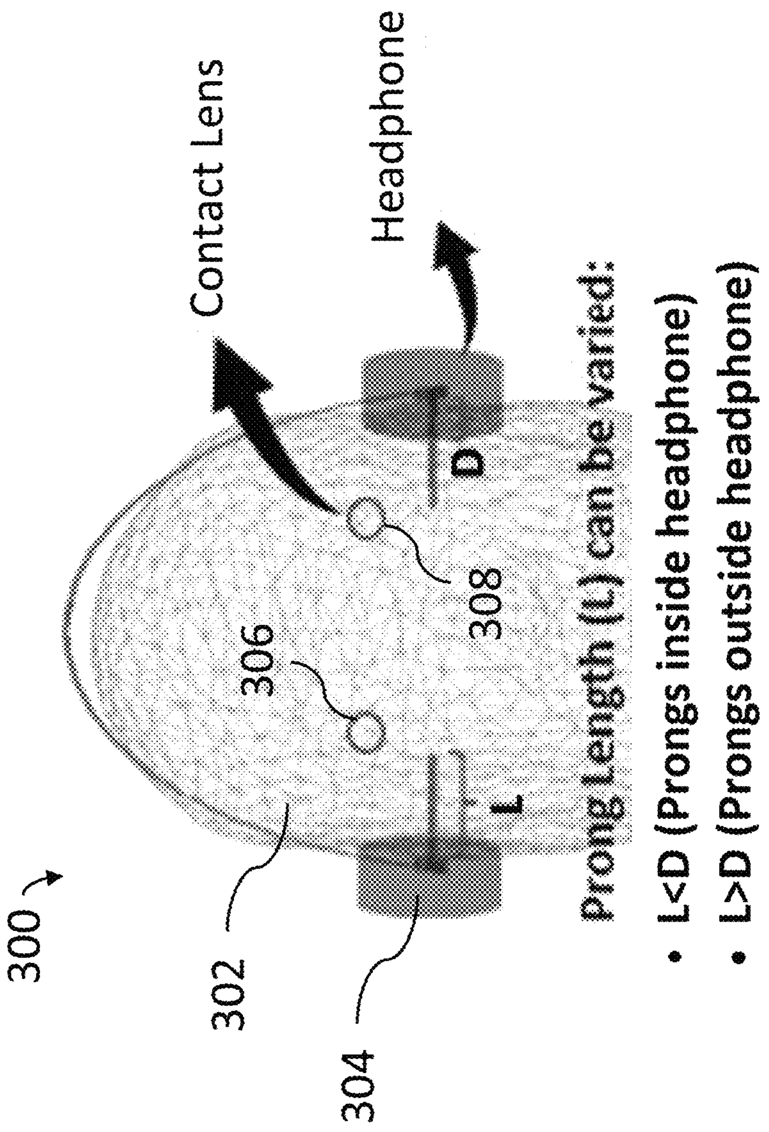
FIG. 2A depicts a schematic of one exemplary galvanic EQS-HBC system, showing a headset as a signal transmitter and smart contact lenses as signal receivers.
Figure 2B:
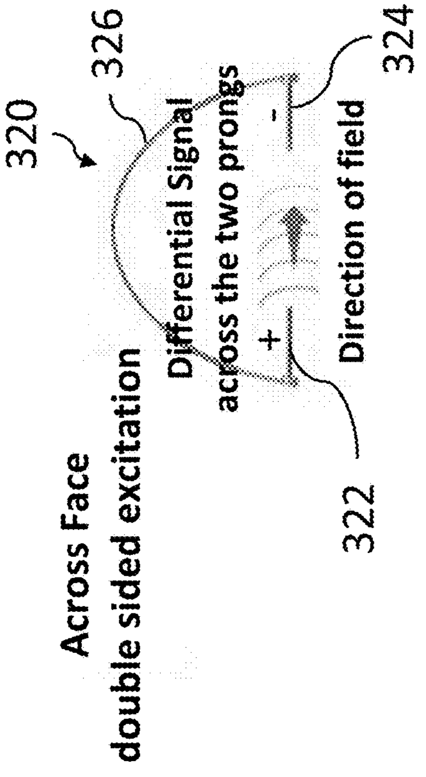
FIG. 2B depicts a schematic of a first embodiment of a headset operable with the galvanic EQS-HBC system of FIG. 2A.
Figure 2C:
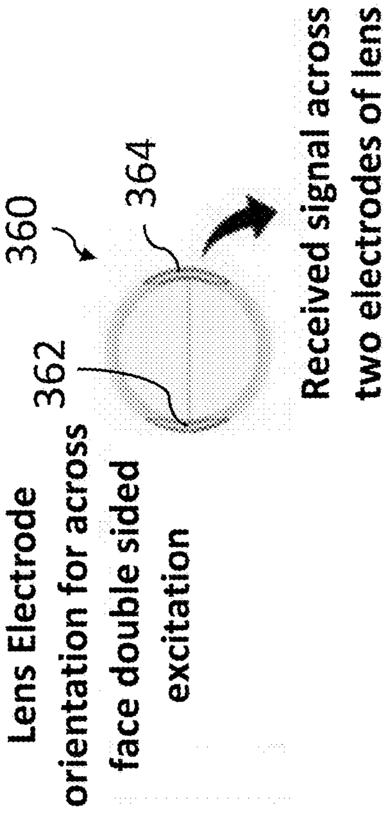
FIG. 2C depicts a schematic of a first embodiment of smart contact lenses operable with the headset of FIG. 2B.
Figure 2D:
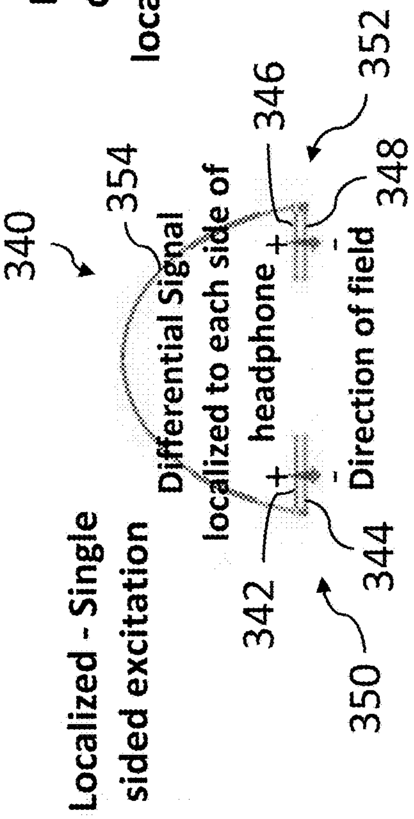
FIG. 2D depicts a schematic of a second embodiment of a headset operable with the galvanic EQS-HBC system of FIG. 2A.
Figure 2E:
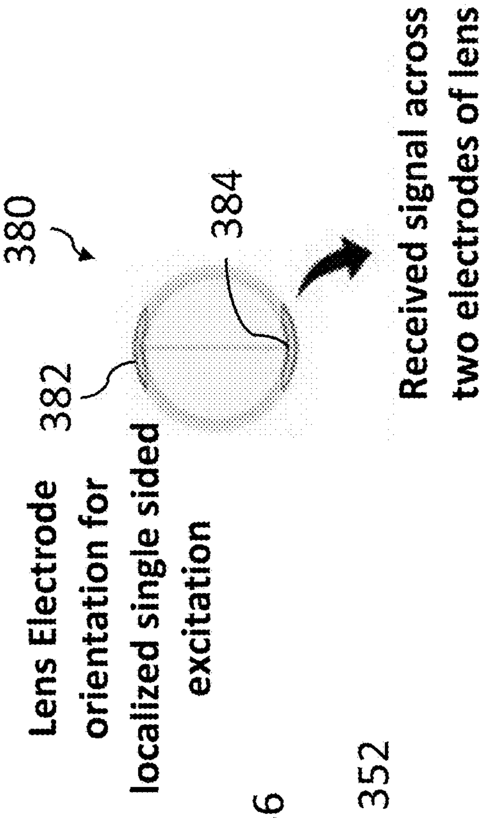
FIG. 2E depicts a schematic of a second embodiment of smart contact lenses operable with the headset of FIG. 2D.

The application of galvanic EQS-HBC communication methodology for wearable to implantable communication, as illustrated in FIG. 1D, may be implemented on FEM based EM solver Ansys HFSS using one or more of the simulation models illustrated in FIGS. 2A-2E. Specifically, FIG. 2A shows one exemplary experiment (300) where a human head model (e.g., a VHP Female model from NEVA EM) (302) is used to emulate the human body along with the transmitter headset (304) and the receiver contact lenses (306, 308). The dielectric properties of human body tissues may be taken from the known sources for modeling, such as from database by Gabriel et al. ("Tissue Properties from Gabriel-Gabriel Model," available at the URL <https://itis.swiss/virtual-population/tissue-properties/database/dielectric-properties/>.) As shown in the first transmitter embodiment (320) of FIG. 2B and the second transmitter embodiment (340) of FIG. 2D, the transmitters, which may be positioned on or within a headset, may be excited via an AC voltage excitation with a source resistance. Specifically, the method of differential excitation varies between the two embodiments shown in FIGS. 2B and 2D. Further, two alternative contact lens embodiments (360, 380) are illustrated in FIGS. 2C and 2E, respectively, and the utilized embodiment may be selected based upon the direction of the electrical fields generated by the transmitter embodiment (320 or 340), as will be described below. In the described experiments, a frequency range of 10 kHz to 100 MHz was utilized, which falls within the EQS region, and a source resistance may be swept from 10 ohms to 10 kilo-ohms.

In the first headset embodiment (320) of FIG. 2B, opposing single prongs (322, 324) on each side of the headset (326) generate the differential voltage excitation horizontally across the face of the person. Accordingly, as transmitter prongs (322, 324) generate the electric field oriented horizontally relative to the headset wearer's face, contact lens embodiment (360), as shown in FIG. 2C, may be utilized to detect the potential difference. Contact lens (360) may be shaped and sized to emulate a common contact lens and may include electrodes (362, 364) positioned diametrically opposite to each other to maximize the potential defined between the electrodes (362, 364). More particularly, electrodes (362, 364) are oriented horizontally so as to match that of the electric field to maximize the potential defined between them.

In the second headset embodiment (340) of FIG. 2D, two prongs (342, 344, 346, 348) coming out of each side (350, 352), respectively, of the headset (354) generate localized differential excitations vertically across the face of the person. Accordingly, as transmitter prongs (342, 344, 346, 348) generate the electric fields oriented vertically relative to the headset wearer's face, contact lens embodiment (380), as shown in FIG. 2E, may be utilized to detect the potential differences of the fields. Contact lens (380) may be shaped and sized to emulate a common contact lens and may include electrodes (382, 384) positioned diametrically opposite to each other to maximize the potential defined between the electrodes (382, 384). More particularly, electrodes (382, 384) are oriented vertically so as to match that of the electric field to maximize the potential defined between them.

Figure 3B:
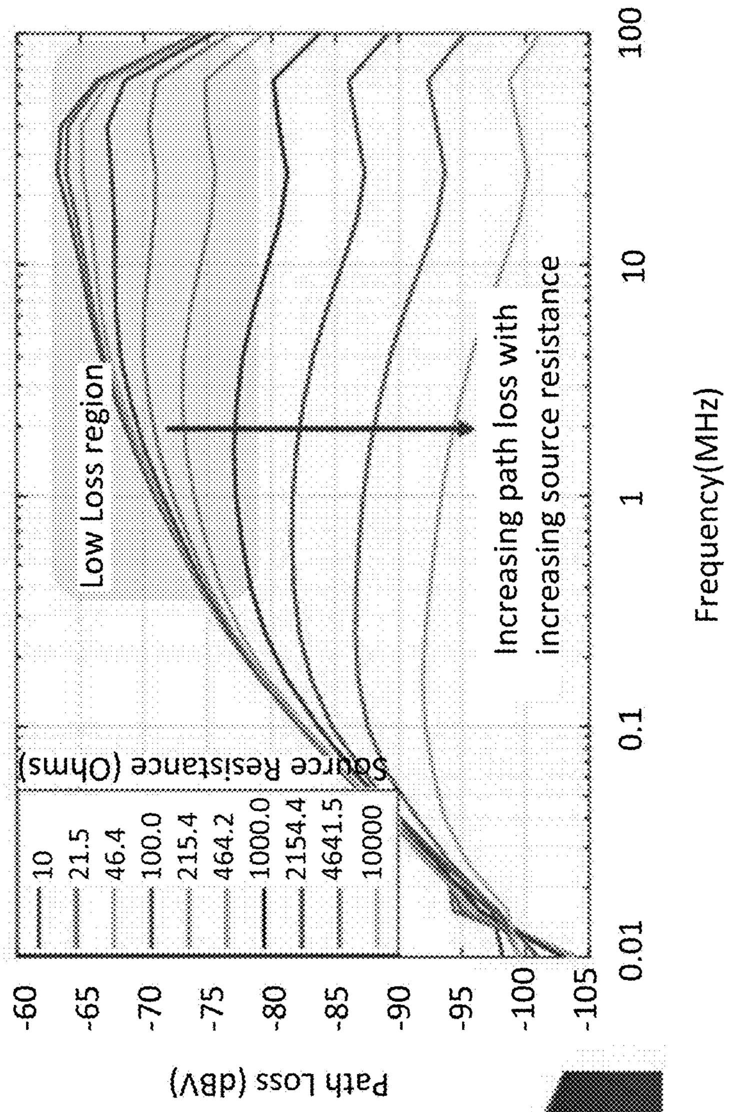
FIG. 3B depicts a graphical representation of experimental results generated by the practical application of the galvanic EQS-HBC system of FIG. 3A.
Figure 3A:
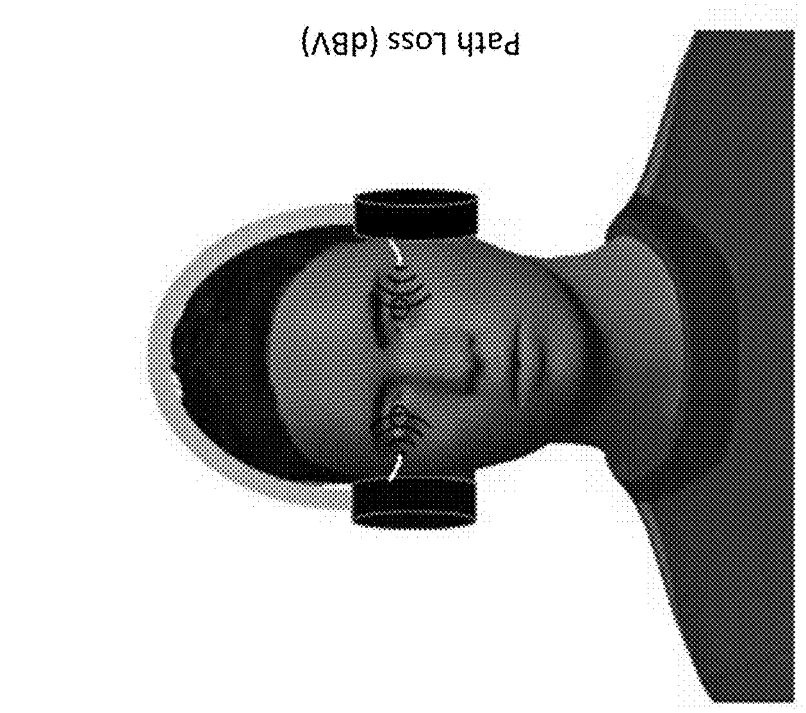
FIG. 3A depicts a schematic of a practical application of the galvanic EQS-HBC system formed by the utilization of the headset of FIG. 2B and the contact lenses of FIG. 2C.

FIG. 3A illustrates the application of the embodiment described above with reference to FIGS. 2B and 2C, which utilizes a two-sided (i.e., horizontal) excitation being performed using prongs placed on opposing sides of the head to effectively excite the human body to provide an electric field horizontally across the head that is captured by one or more of the receiving contact lenses. More particularly, the transmitted electric fields are aligned with horizontally positioned electrodes of the contact lens (e.g., electrodes (362, 364) of lens (360)) relative to the eye. The length of the prongs may be varied as necessary to optimize the received voltage strength by aligning the transmitted fields with the electrodes of the contact lens. FIG. 3B shows the received signal strength as measured relative to the frequency for the application of FIG. 3A with the source resistance as one parameter. The results of FIG. 3B illustrate that, for a low source resistance (e.g., RS≈10 ohms), the path loss can be as low as around 65 dB for frequency of operation at tens of megahertz.

Figure 4B:
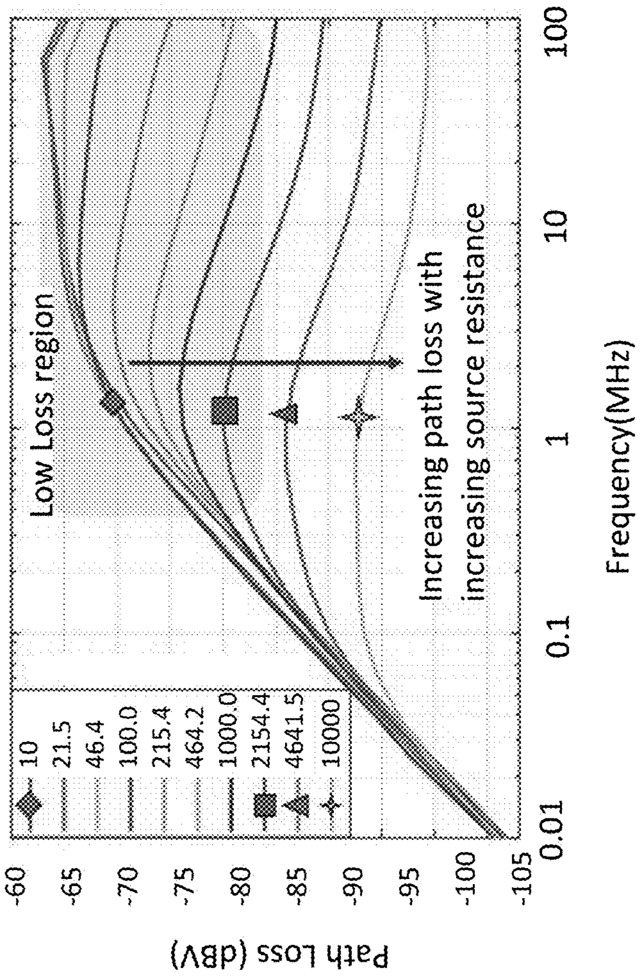
FIG. 4B depicts a graphical representation of experimental results generated by the practical application of the galvanic EQS-HBC system of FIG. 4A.
Figure 4A:
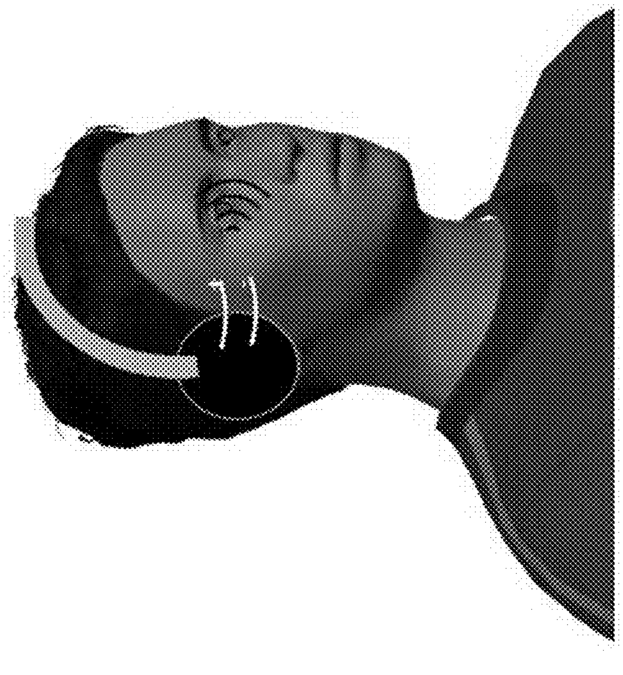
FIG. 4A depicts a schematic of a practical application of the galvanic EQS-HBC system formed by the utilization of the headset of FIG. 2D and the contact lenses of FIG. 2E.

FIG. 4A illustrates the application of the embodiment described above with reference to FIGS. 2D and 2E, which utilizes one or more single-sided (i.e., vertical) excitations being performed using one or more sets of prongs placed on the side of the head to effectively excite the human body to provide one or more electric fields vertically across the head that is captured by one or more of the receiving contact lenses. More particularly, the transmitted electric fields are aligned with vertically positioned electrodes of the contact lens (e.g., electrodes (382, 384) of lens (380)) relative to the eye. The length of the prongs may be varied as necessary to optimize the received voltage strength by aligning the transmitted fields with the electrodes of the contact lenses. FIG. 4B shows the received signal strength as measured relative to the frequency for the application of FIG. 4A with the source resistance as one parameter. The results of FIG. 4B illustrate that, for a low source resistance (e.g., RS≈10 ohms), the path loss can be as low as around 50 dB for frequency of operation at tens of megahertz.

Reference systems that may be used herein can refer generally to various directions (for example, upper, lower, forward and rearward), which are merely offered to assist the reader in understanding the various embodiments of the disclosure and are not to be interpreted as limiting. Other reference systems may be used to describe various embodiments, such as those where directions are referenced to the portions of the device, for example, toward or away from a particular element, or in relations to the structure generally (for example, inwardly or outwardly).

While examples, one or more representative embodiments and specific forms of the disclosure have been illustrated and described in detail in the drawings and foregoing description, the same is to be considered as illustrative and not restrictive or limiting. The description of particular features in one embodiment does not imply that those particular features are necessarily limited to that one embodiment. Some or all of the features of one embodiment can be used in combination with some or all of the features of other embodiments as would be understood by one of ordinary skill in the art, whether or not explicitly described as such. One or more exemplary embodiments have been shown and described, and all changes and modifications that come within the spirit of the disclosure are desired to be protected.

What is claimed is:

1. A system, comprising:

(a) a wearable device including one or more signal transmitters, wherein the wearable device is configured to be positioned adjacent to or in contact with a human or animal body;

(b) an implantable device including a signal receiver, wherein the implantable device is configured to be implanted onto or within the human or animal body, wherein the one or more signal transmitters of the wearable device are configured to transmit signals through the human or animal body to the signal receiver of the implanted device via a galvanic coupling operable using electro-quasistatic signal transmission; and (c) a capacitive element comprising an earpad that includes a dielectric material, the capacitive element being positioned on an electrical current flow path of the galvanic coupling defined between at least one of the one or more signal transmitters and the signal receiver, wherein the capacitive element is configured to restrict flow of direct current (DC) power between the at least one of the one or more signal transmitters and the signal receiver.

2. The system of claim 1, wherein the wearable device includes a headset, headband, cap, helmet, spectacles, or headgear.

3. The system of claim 1, wherein the implantable device includes at least one of a contact lens, cochlear implant, implantable device inside a mouth, or neural implant inside a brain.

4. The system of claim 1, wherein the capacitive element includes a series capacitor configured to restrict DC power being transmitted by the one or more signal transmitters.

5. The system of claim 4, wherein the series capacitor is embedded within the wearable device.

6. The system of claim 1, wherein the signal transmitters include one or more prongs configured to excite the human or animal body and generate path losses of 50 dB to 65 dB.

7. The system of claim 1, wherein the earpad is configured to couple to an exterior of the wearable device, and the dielectric material is configured to restrict the flow of the DC power between the at least one of the one or more signal transmitters and the signal receiver.

8. The system of claim 1, wherein the one or more signal transmitters are configured to transmit signals to the signal receiver within a frequency range of 10 KHz to 100 MHz.

9. The system of claim 1, wherein the wearable device includes a first signal transmitter defined by two prongs adapted to be positioned on the same side of a head of the human or animal, wherein the two prongs are configured to generate a differential electric signal polarized vertically relative to a head of the human or animal.

10. The system of claim 9, wherein the implantable device includes a contact lens sized for placement onto an eye of the human or animal, wherein the contact lens includes a pair of electrodes positioned vertically opposite to each other relative to the eye, wherein the electrodes are configured to receive the differential electric signal.

11. The system of claim 1, wherein the wearable device includes a signal transmitter defined by first and second prongs adapted to be positioned on opposing sides of a head of the human or animal, wherein the first and second prongs are configured to generate a differential electric signal polarized horizontally relative to the head of the human or animal.

12. The system of claim 11, wherein the implantable device includes a contact lens sized for placement onto an eye of the human or animal, wherein the contact lens includes a pair of electrodes positioned horizontally opposite to each other relative to the eye, wherein the electrodes are configured to receive the differential electric signal.

13. A system comprising:

(a) a wearable device including one or more signal transmitters, wherein the wearable device is configured to be positioned adjacent to or in contact with a human or animal body;

(b) an implantable device including a signal receiver, wherein the implantable device is configured to be implanted onto or within the human or animal body, wherein the one or more signal transmitters of the wearable device are configured to transmit signals through the human or animal body to the signal receiver of the implanted device via a galvanic coupling operable using electro-quasistatic signal transmission; and (c) a capacitive element positioned on an electrical current flow path of the galvanic coupling defined between at least one of the one or more signal transmitters and the signal receiver, wherein the capacitive element is configured to restrict flow of direct current (DC) power between the at least one of the one or more signal transmitters and the signal receiver;

wherein the capacitive element includes one or more floating electrodes positioned adjacent to the human or animal body, wherein the one or more floating electrodes are configured to form an air gap operable to restrict the flow of the DC power between the at least one of the one or more signal transmitters and the signal receiver.

14. The system of claim 13, wherein the wearable device includes a waist-mounted device, and wherein the implantable device is positioned inside a stomach of the human or animal.

15. A system, comprising:

(a) a wearable headset including one or more signal transmitters, wherein the wearable headset is configured to be positioned adjacent to or in contact with a head of a human or animal body and generate an electric field across the head of the human or animal; and (b) a contact lens including a signal receiver, wherein the contact lens is configured to be positioned on an eye of the human or animal body, wherein the contact lens includes a pair of electrodes configured to sense a potential difference defined by the electric field;

wherein the one or more signal transmitters are configured to communicate through the human or animal body with the signal receiver via a galvanic coupling utilizing electro-quasistatic signal transmission; and (c) a capacitive element comprising an earpad including a dielectric material, the capacitive element being positioned on an electrical current flow path of the galvanic coupling defined between at least one of the one or more signal transmitters and the signal receiver, wherein the capacitive element is operable to restrict flow of direct current (DC) power between the at least one of the one or more signal transmitters and the signal receiver.

16. The system of claim 15, wherein the one or more signal transmitters are formed by one or more prongs embedded within the wearable headset, wherein the capacitive element includes a plurality of the earpad each configured to couple to an exterior of the wearable headset, wherein each earpad includes a dielectric material configured to restrict flow of the DC power between the at least one of the one or more signal transmitters and the signal receiver.

17. The system of claim 15, wherein:

(a) the wearable headset includes a first signal transmitter defined by two prongs adapted to be positioned on the same side of the head of the human or animal, the two prongs configured to generate the electric field polarized vertically relative to the head of the human or animal; and (b) the pair of electrodes of the contact lens are positioned vertically opposite to each other relative to the eye of the human or animal.

18. The system of claim 15, wherein:

(a) the wearable headset includes a first signal transmitter defined by first and second prongs adapted to be positioned on opposing sides of a head of the human or animal, wherein the first and second prongs are configured to generate the electric field polarized horizontally relative to the head of the human or animal; and (b) the pair of electrodes of the contact lens are positioned horizontally opposite to each other relative to the eye.

19. A system operable for human body communication, comprising:

(a) a wearable device including one or more signal transmitters, wherein the wearable device is configured to be positioned adjacent to or in contact with a human or animal body;

(b) a contact lens including a pair of electrodes, wherein the contact lens is configured to be implanted onto an eye of the human or animal body, wherein the signal transmitter of the wearable device is configured to transmit signals through the human or animal body to the pair of electrodes of the contact lens via a galvanic coupling operable using electro-quasistatic signal transmission within a frequency range of 10 KHz to 100 MHz; and (c) a capacitive element positioned on an electrical flow path of the galvanic coupling defined between at least one of the one or more signal transmitters and pair of electrodes, wherein the capacitive element comprises at least one of (i) a floating electrode to form an air gap and (ii) an earpad including a dielectric material, the air gap and/or the dielectric material configured to restrict the flow of direct current (DC) power between the at least one of the one or more signal transmitters and the pair of electrodes.

* * * * *